United States Patent [19]

Kydonieus et al.

[11] Patent Number: 5,468,501
[45] Date of Patent: * Nov. 21, 1995

[54] ARTICLE USEFUL FOR ADMINISTRATION OF PHARMACOLOGICALLY-ACTIVE SUBSTANCES TRANSDERMALLY, ORALLY OR BY MEANS OF IMPLANT

[75] Inventors: Agis Kydonieus, Kendall Park; Kishore R. Shah, Bridgewater, both of N.J.; Bret Berner, Ardsley on Hudson, N.Y.

[73] Assignee: Hercon Laboratories Corporation, New York, N.Y.

[*] Notice: The portion of the term of this patent subsequent to Jul. 19, 2005, has been disclaimed.

[21] Appl. No.: 385,205

[22] Filed: Feb. 8, 1995

Related U.S. Application Data

[63] Continuation of Ser. No. 974,672, Nov. 10, 1992, abandoned, which is a continuation of Ser. No. 503,600, Apr. 3, 1990, abandoned, which is a continuation of Ser. No. 16,796, Feb. 20, 1987, abandoned, which is a continuation-in-part of Ser. No. 847,635, Apr. 3, 1986, Pat. No. 4,758,434, which is a continuation-in-part of Ser. No. 657,911, Oct. 5, 1984, abandoned, which is a continuation-in-part of Ser. No. 413,658, Sep. 1, 1982, abandoned.

[51] Int. Cl.⁶ ........................................ A61F 13/00
[52] U.S. Cl. .................. 424/443; 429/448; 429/449
[58] Field of Search ................................. 424/443, 448, 424/449

[56] References Cited

U.S. PATENT DOCUMENTS

| | | | |
|---|---|---|---|
| 3,634,023 | 1/1972 | Foote | 524/226 |
| 3,857,934 | 12/1974 | Bernstein et al. | 424/411 |
| 3,911,135 | 10/1975 | Tupak et al. | 424/78 |
| 3,921,636 | 11/1975 | Zaffaroni | 424/432 |
| 3,965,255 | 6/1976 | Bloch et al. | 424/450 |
| 3,996,934 | 12/1976 | Zaffaroni | 424/434 |

(List continued on next page.)

FOREIGN PATENT DOCUMENTS

| | | |
|---|---|---|
| 314738 | 3/1974 | Austria . |
| 930668 | 7/1973 | Canada . |
| 10139127 | 5/1985 | European Pat. Off. . |
| 2314509 | 9/1973 | Germany . |
| 2362123 | 6/1974 | Germany . |
| 2309202 | 8/1974 | Germany . |
| 59-84816 | 5/1984 | Japan . |
| 620122 | 11/1980 | Switzerland . |
| 2155335 | 9/1985 | United Kingdom . |

OTHER PUBLICATIONS

H. Mark et al.: "Encyclopedia of Polymer Science and Technology; Plastics, Resins, Rubbers, Fibers", vol. 10, 1969, J. Wiley, New York, US; p. 269.

Japanese Patents Gazette, Section Ch: Chemical, Week E37, 1982, ref. No. 77553, Derwent Publications, London, GB; for JP-A-57-126416 (Sekisui Chemi Ind K.K.) Aug. 06, 1982.

Chemical Abstracts, vol. 101, Nov. 1984, Columbus, Ohio, USA for J. Szlaski and Z. Zakrzewski, "Sustained-action propranolol tablets", p. 387, col. 2, abstract No. 177448g & Acta Pol. Pharm. 1983 40(5-6), 615-620.

Patent Abstracts of Japan, unexamined applications, C section, vol. 10, No. 49, Feb. 26, 1986, p. 31 C 330, for Kokai-No. 60-193 918 (Mitsui Toatsu Kagaku K.K.).

*Primary Examiner*—D. Gabrielle Phelan
*Attorney, Agent, or Firm*—Sughrue, Mion, Zinn, Macpeak & Seas

[57] ABSTRACT

A device useful for administration of pharmacologically-active substances transdermally, orally, or by means of subdermal implant includes an impermeable backing layer, a plasticized polyvinyl chloride layer, and an adhesive layer, wherein the plasticized polyvinyl chloride layer includes from about 20 up to about 70% by weight of a polyvinyl chloride resin, from about 20 up to about 70% by weight of a plasticizer, and from about 0.5 up to about 35% by weight of a pharmacologically-active substance such as isosorbide dinitrate, nicotine, clonidine, guanfacine, indomethacin, nitroglycerin, and prostaglandin and optionally excipients.

32 Claims, 8 Drawing Sheets

U.S. PATENT DOCUMENTS

| | | | |
|---|---|---|---|
| 4,150,109 | 4/1979 | Dick et al. | 424/411 |
| 4,605,548 | 8/1986 | Ushiyama | 424/449 |
| 4,699,777 | 12/1987 | Zupon et al. | 424/449 |
| 4,712,460 | 12/1987 | Allen et al. | 424/443 |
| 4,758,434 | 7/1988 | Kydonieous | 424/449 |
| 4,797,283 | 1/1989 | Allen et al. | 424/443 |

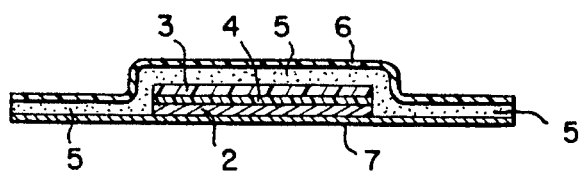
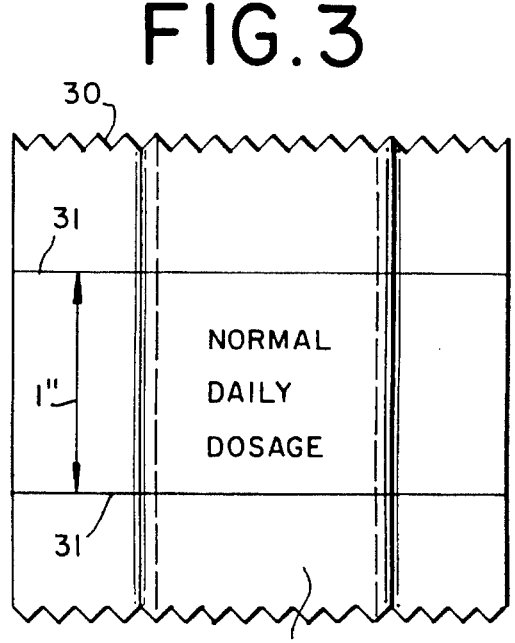
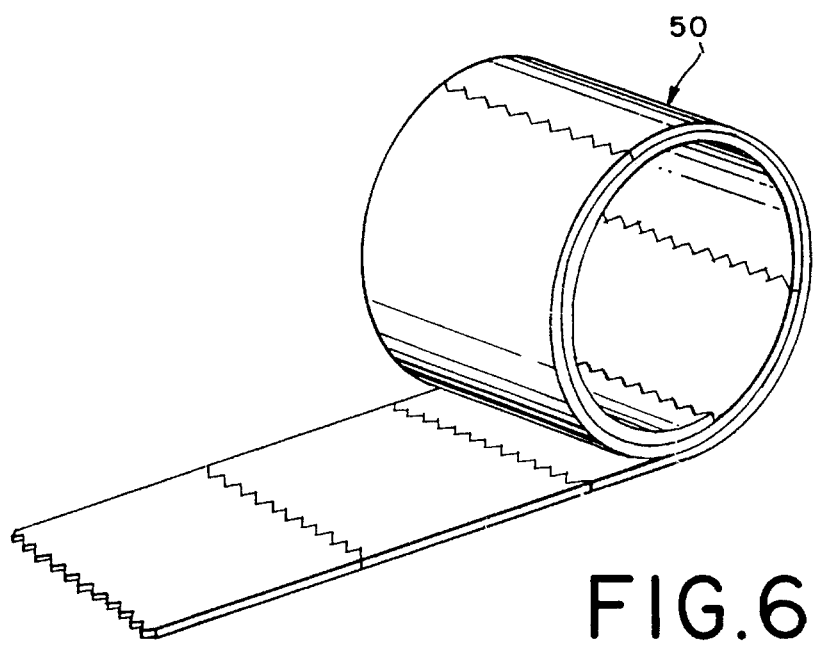

IR SPECTRUM

ARTICLE USEFUL FOR ADMINISTRATION OF PHARMACOLOGICALLY-ACTIVE SUBSTANCES TRANSDERMALLY, ORALLY OR BY MEANS OF IMPLANT

This application is a continuation of application Ser. No. 07/974,672 filed Nov. 10, 1992, now abandoned which is a continuation of application Ser. No. 07/503,600 filed Apr. 3, 1990, now abandoned which is a continuation of application Ser. No. 07/016,796 filed Feb. 20, 1987 now abandoned, which is a continuation-in-part of U.S. patent application Ser. No. 847,635 filed on Apr. 3, 1986 now U.S. Pat. No. 4,758,434 which, in turn, is a continuation-in-part of U.S. patent application Ser. No. 657,911 filed on Oct. 5, 1984 now abandoned which, in turn, is a continuation-in-part of U.S. patent application Ser. No. 413,658 filed on Sep. 1, 1982 now abandoned.

BACKGROUND OF THE INVENTION

1. Field of the Invention

This invention relates broadly to articles of manufacture for administration of pharmacologically-active substances, transdermally, orally and by means of implant (e.g., subdermal implant). The devices consist essentially of a vinyl chloride polymer or copolymer of vinyl chloride containing a majority of vinyl chloride monomeric units and a small amount of other vinyl monomeric units, e.g., vinyl acetate, and intimately dispersed therewith at least one of said pharmacologically-active agents and a plasticizer. Examples of pharmacologically-active agents are isosorbide dinitrate, nicotine, indomethacin, clonidine, glyceryl trinitrate, guanfacine and prostaglandin. Contemplated within the scope of this invention are devices for the controlled release and transdermal administration of such pharmacologically-active agents as nitroglycerine (e.g., in the treatment of conditions, e.g., angina pectoris).

2. The Prior Art

Many prior art articles of manufacture have been disclosed for controlled release delivery of various drugs including transdermal delivery of nitroglycerin. In general, however, available commercial devices and indeed devices published in the prior art are limited with respect to rate of delivery of pharmacologically-active substance.

Canadian Patent No. 930,668 discloses a bandage for administering drugs comprised of a backing member, a pressure sensitive adhesive, and at least one reservoir disposed between the backing member and pressure sensitive adhesive. The reservoir is comprised of a systemically active drug formulation confined within a wall member, the wall member being formed from a drug release rate controlling material. The reservoir can be in the form of discrete microcapsules or distinct reservoir compartments or layers. The reservoir can also be in the form of walled containers having one or more interior drug-containing chambers, as well as solid matrices having a systemically active drug distributed therethrough. The Canadian patent discloses a wide variety of materials which can be used to form the reservoir. Among the materials mentioned are silicone rubbers, hydrophilic polymers of monoesters of an olefinic acid, polyvinylalcohol, polyvinylacetate, plasticized polyvinylchloride, plasticized nylon, collagen, modified collagen, gelatin, and waxes such as polyethylene wax, oxidized polyethylene wax, hydrogenated castor oil and the like, with the silicone rubbers being preferred. The Canadian patent does not contain any examples showing the use of plasticized polyvinyl chloride.

Similarly, Zaffaroni, U.S. Pat. No. 3,921,636 issued on Nov. 25, 1975 discloses a drug delivery device for administering a drug at a controlled rate for a prolonged period of time comprising a plurality of reservoirs containing drug distributed through a matrix. The reservoirs and the matrix are formed of materials permeable to passage of the drug. The rate of drug permeation from the reservoir is lower than the rate of permeation through the matrix so that release from the reservoir is the drug release rate controlling step. Thus, Example 6, at column 15, lines 5–30 of U.S. Pat. No. 3,921,636 relates to a polyvinyl chloride resin containing plasticizer and prednisolone disodium phosphate thusly:

"A drug delivery device for the controlled, oral administration of water-soluble prednisolone is prepared as follows: first, a plurality of drug reservoirs comprising porous, discrete particles of polymerized poly(vinyl chloride) of about 100 microns diameter are prepared by mixing 100 g of suspension grade poly(vinyl chloride) resin with 50 g of octyl diphenyl phosphate and 10 g of prednisolone disodium phosphate at room temperature into a sticky, wet mass. Next, the temperature of the mixture is raised to 80° C. for about 3 to 7 minutes, while stirring, to form dry, free flowing discrete drug reservoirs. The reservoirs are uniformly dispersed through a matrix by mixing 50 g of reservoirs containing the prednisolone with 140 g of polydimethylsiloxane, 10 g of silicone oil, and 0.5 g of stannous octoate. After mixing the ingredients, the mixture is charged into pill mods and allowed to cure for 30 minutes. Oral administration of the resulting device yields a controlled essentially constant rate of release of prednisolone phosphate to the gastrointenstinal tract to give a more uniform blood level of prednisolone over a longer period of time than is achieved when prednisolone alcohol is administered by standard prior art pills."

U.S. Pat. No. 4,150,109 (Dick, et al) issued on Apr. 17, 1979 entitled "Devices for Protecting Animals from Ectooarasites" discloses and claims:

"In an animal collar for controlling fleas and ticks on cats and dogs, a part of said animal collar being formed of a solid vinyl or vinylidene polymer matrix in which is dispersed a pesticidal composition, an improved pesticidal composition consisting essentially of:

(a) 0.5 to 15% by weight of an ethylenically unsaturated oil, and (b) a mixture of diethyl 0-(2-isopropyl-4-methyl- 6-pyrimdinyl)thionophosphate and diethyl 0-(2-isopropyl-4-methyl-6-pyrimidinyl)phosphate, wherein diethyl 0-(2-isopropyl-4-methyl-6-pyrimidinyl) thionophosphate is 10 to 90% by weight of said mixture and diethyl 0-(2-isopropyl-4-methyl-6-pyrimidinyl)phosphate is 90 to 10% by weight of said mixture."

wherein the "solid vinyl . . . matrix" and the plasticizers are
described thusly: "The macromolecular substance preferably has a weight of more than 1000; it is selected from the homopolymers and copolymers obtained starting from vinyl chloride, vinyl acetate, vinyl acetals, vinylalcohol, vinylbenzene and divinylbenzene and vinylidene chloride; the copolymers may, in addition, contain additional components such as ethylenic, propylenic, butadienic, isoprenic, acrylic and methacrylic components.

Preferably, the macromolecular substance is a polymer or copolymer of a vinyl compound such as, for example, the polyvinyl halides. The particularly preferred macromolecular substances are polymers or copolymers of vinyl chloride.

The macromolecular substance preferably contains one or more plasticizers.

The plasticizers are liquid esters with a vapour pressure of less than 0.0001 mm/Hg at 25° C. Some nonrestrictive examples of plasticizers are: diethyl, dimethyl, dipropyl, dibutyl, dihexyl, dioctyl and didecyl phthalate, dibutyl, diamyl, dinonyl, dioctyl, and didecyl adipate, dipropyl, dibutyl, dibenzyl and dioctyl sebacate, diethyl, dipropyl and dibutyl citrate, triphenyl and tricresyl phosphate and the triglycerides.

The preferred plasticizers are dibutyl phthalate and dioctyl adipate, which make it possible to obtain an arrangement with good flexibility, on the surface of which the active principle appears rapidly and regularly."

Furthermore, as is well known, polyvinyl chloride (PVC) is never used alone, but is always mixed with other ingredients before being processed. Polyvinyl chloride appeared initially to be an unpromising resin because of its thermal instability and high rigidity. PVC, however, was then discovered to form a rubber-like material when dissolved hot in high boiling solvents known as plasticizers and cooled to room temperature. PVC is now available in a number of different physical forms and types, and its manufacture depends on the form desired. Thus, PVC is available as a vinyl latex, a dispersion resin, or a general purpose resin. PVC latexes are true colloidal dispersions of submicrometer particles in water, stabilized by a surfactant system, and need plasticizers in order to form a continuous film. The PVC in vinyl latex is manufactured by emulsion polymerization.

Dispersion resins are produced by emulsion polymerization and are mixed with plasticizers to form a colloidal dispersion. Such dispersions are known as plastisols and are easily handled and readily pourable. When heated to a temperature of about 148° to 177° C. the plastisol is transformed to a homogeneous melt which, upon cooling to below 50° C., results in a tough flexible product. The PVC resins made by emulsion polymerization are hard spheres of particle size between about 0.05 and 20 microns, such as between 1 and 20 microns. They do not have the ability to absorb plasticizers. Therefore, a mixture containing, for example, 30% plasticizer and 70% PVC resin, produces a flowable liquid, known as "plastisol".

General purpose PVC resins are made by mass and suspension polymerization process, and comprise the largest amount of PVC resins produced, such as at least 80% of all PVC resins, and are used chiefly to make so-called 100% vinyl products by a variety of molding and extrusion techniques. Resins intended for flexible applications should have good uptake of plasticizer in a dry blending operation and contain more than 25% of a plasticizer system. PVC compounds that contain less than 25% plasticizers are referred to as semirigid compounds. The PVC resins manufactured by suspension and bulk polymerization are 50 to 200, such as 100 to 150 microns in diameter, and are like sponges. They are capable of absorbing large amounts of plasticizers, so that even a 50% plasticizer, 50% PVC resin composition would result in a non-flowing, solid material.

SUMMARY OF THE INVENTION

It is an object of the present invention to provide an article of manufacture which offers enhanced delivery capability of pharmacologically-active agents over prior commercial devices (transdermal devices, articles used to orally administer pharmacologically-active agents and subdermal implants used to administer subdermally pharmacologically-active agents) by providing an article capable of efficaciously administering pharmacologically-active agents such as isosorbide, dinitrate, nicotine, indomethacin, clonidine, glyceryl trinitrate, guanfacine, and prostaglandin directly from a plastisol resin layer in which the pharmacologically-active agent is incorporated in relatively high concentrations, e.g., from 0.5 up to 35%.

This invention also enables the administration of a pharmacologically-active agent, such as isosorbide dinitrate, nicotine, indomethacin, clonidine, glyceryl trinitrate, guanfacine, and prostaglandin to be achieved through an article of manufacture, e.g., a transdermal delivery device requiring contact with a relatively smaller area of a patient's tissue, such as the epidermis in the case of a transdermal delivery device.

This, this invention is directed to an article of manufacture incorporating a plasticized polyvinyl chloride resin monolayer for administration of pharmacologically-active agents transdermally, orally or by means of subdermal implant to a patient requiring treatment for a condition such as, for example, angina pectoris (in the case of the use of such materials as nitroglycerin). In particular, it has been found that pharmacologically-active agents such as isosorbide dinitrate, nicotine, indomethacin, clonidine, glyceryl trinitrate, guanfacine and prostaglandin can be homogeneously dispersed in high concentrations in polymerized polyvinyl chloride resin and plasticizer; the composition is fused into a solid layer and the layer is applied onto the tissue of a patient (either transdermally, orally or subdermally) whereby the pharmacologically-active agent is absorbed either (i) through the patient's skin or (ii) through the patient's internal membranes or (iii) directly into the circulation system.

A preferred embodiment comprises a multilayer adhesive bandage device incorporating a plastisol monolayer containing homogeneously dispersed pharmacologically-active agents, e.g., isosorbide dinitrate, nicotine, indomethacin, clonidine, glyceryl trinitrate, guanfacine and prostaglandin.

BRIEF DESCRIPTION OF THE DRAWINGS

FIG. 1 is a cross-sectional view of a preferred pharmacologically-active agent delivery device in accordance with this invention.

FIG. 2 is a plan view of a strip of material in accordance with this invention viewed from the surface which is applied to the patient's skin.

FIG. 3 is a plan view of material in accordance with this invention viewed from the surface away from the surface which is applied to the patient's skin.

FIG. 6 is a perspective view of a roll of material in accordance with this invention.

Figure 4:
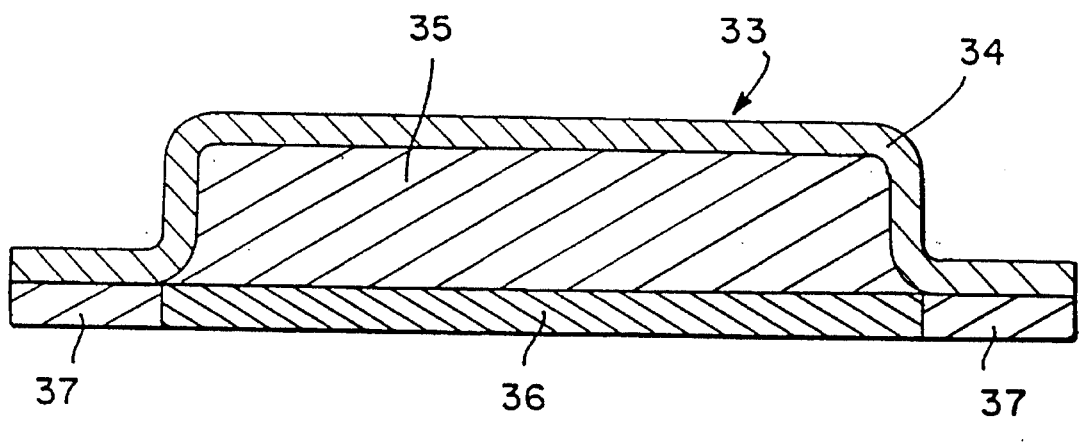
FIG. 4 is an enlarged sectional schematic view of a specific embodiment of the invention; a transdermal device for controlled release of a pharmacologically-active agent from a plasticized polyvinyl chloride monolayer through a membrane transdermally.

Example 12 is the infrared spectrum of ADMEX® 760 as used in Examples II–XIX.

DETAILED DESCRIPTION OF THE INVENTION

The invention is described herein with respect to preferred embodiments including transdermal devices containing various pharmacologically-active agents including, but not limited to, indomethacin having the structure:

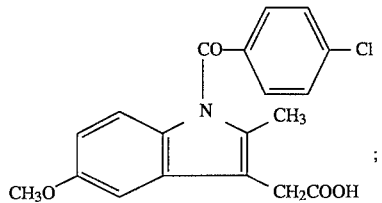

guanfacine having the structure:

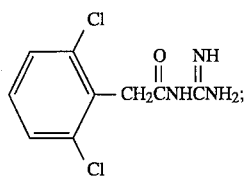

clonidine having the structure:

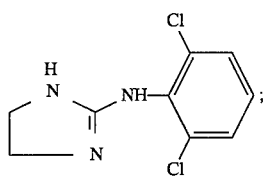

nicotine having the structure:

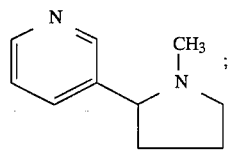

isosorbide dinitrate having the structure:

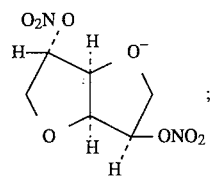

glyceryl trinitrate and prostaglandin (e.g., methyl (±) -(11α, 5z (and 5E), 13E, 16R(and 16S))-16-ethenyl-11,16 dihydroxy-9-oxoprosta-5, 13-dien-1-oate. It will be understood that other embodiments may be employed within the spirit and scope of this invention.

The articles of our invention are useful for transdermal, oral and subdermal administration of pharmacologically-active substances and comprises a solid plasticized polyvinyl chloride (preferably in the form of a "vinyl plastisol-")layer (consisting essentially of polyvinyl chloride and a plasticizer) for contacting a patient's skin or other membrane. The plasticized polyvinyl chloride layer contains from about 20 up to about 70% by weight of a polyvinyl chloride resin which consists essentially of a vinyl chloride polymer containing, predominantly or completely repeating vinyl chloride monomeric units and in an amount of less than about 10% other repeating vinyl units, e.g., repeating vinyl acetate units; from about 20% up to about 70% by weight of the composition of one or more plasticizers; from about 0.5 up to about 0.35% by weight of the total composition of a pharmacologically-active substance, such as isosorbide, dinitrate, nicotine, indomethacin, clonidine, glyceryl trinitrate, guanfacine or prostaglandin and optionally other excipients, such as materials which will accelerate transdermal penetration as exemplified hereinafter. As one example of the use of a pharmacologically-active substance, nitroglycerin can be present in an amount of about 20–35%.

It has now been found that the release rate of an active agent, which is uniformly dispersed in the plasticized polyvinyl chloride layer, is critically dependent upon the proportion of the polyvinyl chloride resin in the composition; and the release follows a bell shaped curve (FIG. 8), the maximum occurring in the range of 30 to 50% PVC content. This is an unexpected finding, which has not hitherto been known. Such a release behavior permits tailoring of release rates of an agent from the matrix.

The reservoir layers of this invention are relatively weak and less than 1500 psi, (FIG. 7), highly flexible and soft materials. In contrast, the flexible vinyl films of commerce are considerably stronger materials exhibiting tensile strengths of the order of 1,500 to 5,000 psi. The polyvinyl chloride resin content of the commercially useful and available flexible vinyl films range from 50 to 75%. Such materials do not have adequate drug permeating characteristics to serve as suitable drug delivery reservoirs.

Referring to FIG. 1, the device 1 includes a solid plastisol monolayer 2 which is composed of or comprises resin, plasticizer and a pharmacologically-active agent as set forth supra.

A formulation for layer 2 may comprise from about 20 up to about 70% by weight of the vinyl resin, from about 20 up to about 70% by weight of plasticizer composition, from about 0.5 up to about 35% by weight of pharmacologically-active agent and the remainder being other excipients, such as materials which will enhance skin penetration. We have found that the substage 1-dodecylhexahydro-2H-azepin-2-one (also known as AZONE® having the structure:

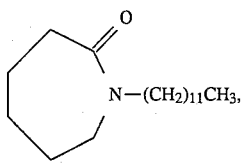

acts as both a plasticizer and as an agent which enhances transdermal penetration of pharmacologically-active agents such as isosorbide dinitrate, indomethacin, and the like as set forth supra. By the same token, N,N-diethyltoluamide having the structure:

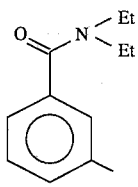

acts in the same manner as AZONE®.

Thus, for example, for a device suitable in the treatment of angina pectoris, a specific formulation for layer 2 comprises about 54% polyvinyl chloride (PVC) resin, about 36% dioctyl phthalate (DOP) plasticizer and 10% nitroglycerin. To prepare layer 2, the PVC and DOP are first blended. Due to the explosive character of the drug, dispersion of the nitroglycerin into the resulting PVC/plasticizer formulation is then carried out under controlled conditions.

The articles of the present invention including the transdermal devices as well as subdermal implants and orally ingested articles of the present invention comprise a plasticized polyvinyl chloride layer and a pharmacologically-active agent uniformly dispersed in the plasticized polyvinyl chloride layer which may be referred to as a reservoir for the pharmacologically-active agent. The polyvinyl chloride reservoir in the present invention is prepared from polyvinyl chloride resin and a primary plasticizer for the resin.

It is preferred that the polyvinyl chloride resins employed in the practice of the present invention are those which are specifically used in preparing polyvinyl chloride "plastisols" namely PVC resins which are made by the well known emulsion polymerization process, which are hard spheres of particle size between 0.05 and 20 microns, such as between 1 and 20 microns, for example, between 1 and 5 microns, or between 0.05 and 1 micron, and which do not have the ability to absorb plasticizers to any great extent. Instead, the plasticizer wets the resin particles at room temperature and only then very slowly penetrates and solvates the resin. These PVC resins when mixed with plasticizers, such as a mixture of 30% primary plasticizer, 70% PVC resin, give a flowable liquid known as plastisol which can then be fused at, for example, approximately 250° F. for approximately 30 seconds to provide a solid polymer layer.

Thus, the PVC resin preferably employed in the present invention is in contrast to the general purpose PVC resins which are produced by suspension or bulk polymerization and which are used in calendering and extrusion processes, which are 50 to 200 microns, such as 100 to 150 microns in diameter, and are like sponges. Thus, the general purpose resins are capable of absorbing large amounts of plasticizers so that even a 50% DOP and 50% PVC resin would result in a non-flowing solid material. The molecular weight of the PVC resins employed in the present invention preferably is a weight average molecular weight between 80,000 and 250,000, such as a weight average molecular weight of 123,000. A suitable polyvinyl chloride resin is one sold by Occidental Chemical Co. under the designation FPC 6338 containing about 96% vinyl chloride monomer units of about 4% vinyl acetate monomer units. Thus, the polyvinyl chloride resin can be a copolymer containing preferably at least 90% by weight vinyl chloride monomer units, such as a copolymer based on vinyl chloride and vinyl acetate.

The polyvinyl chloride resin generally is present in the layer in an amount of 10 to 75 weight percent, preferably 20 to 70 weight percent, based on the total weight of the plasticized PVC composition.

The primary plasticizer which is employed in the present invention can be dioctylphthalate (DOP), benzylbutylphthalate, tri-2-ethylhexylmalaete, dioctyl adipate, epoxidized soybean oil, polymeric adipate plasticizers, which are polymers of adipic acid with a monomer, such as propylene glycol, and for example, can be obtained under the designation Drapex 334F from Witco Chemical Corp., or any other known primary plasticizer for PVC, which is biologically acceptable.

The other examples of polyester adipates, glutarates and sebacates are:

polyester adipate P-644;
polyester glutarate P-530;
polyester glutarate P-540;
polyester glutarate P-550;
polyester glutarate P-7035;
polyester glutarate P-7035M;
polyester glutarate P-7046;
polyester glutarate P-7092; and
polyester sebacate P-1070 manufactured by the C. P. Hall Co., 7300 S. Central Avenue, Chicago, Ill. 60638. Other preferred plasticizers are those which are known as "adipate" plasticizers, for example, ADMEX® 760 which is a high molecular weight (MW= 8000) adipate plasticizer manufactured by the Sherex Division of Nuodex Inc. In general, polyester plasticizers which are polyesters of (i) 1,4-terephthalic acid and/or 1,2-phthalic acid and/or adipic acid with (ii) ethylene glycol or 1,3-propylene glycol having molecular weights in the range of 4000–10,000 are preferred.

Figure 5:
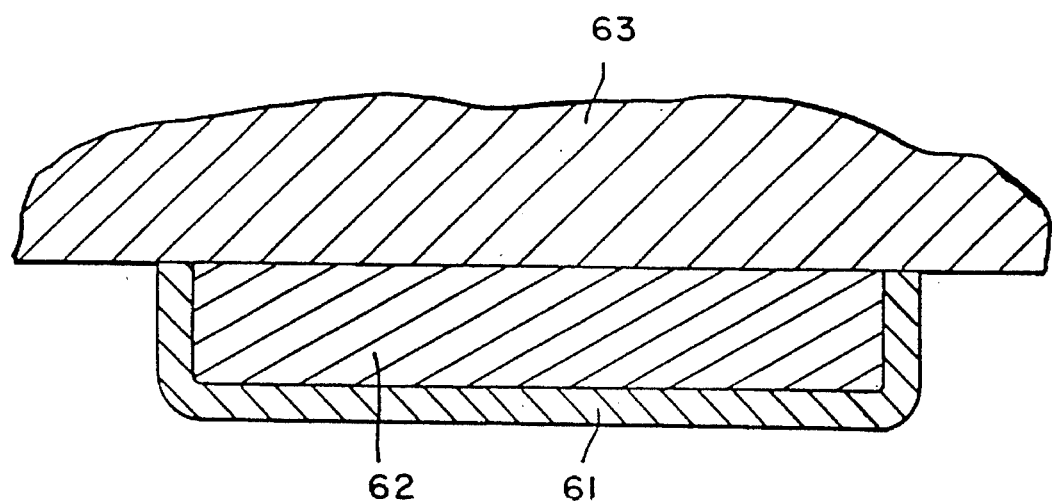
FIG. 5 is an enlarged sectional schematic view of another embodiment of the invention where there is no membrane separating the plasticized polyvinyl chloride monolayer from the epidermis and whereby pharmacologically-active agent is transported from the plasticized polyvinyl chloride transdermally into the patient.

Another preferred plasticizer which also acts as a skin penetrating enhancer for pharmacologically-active drugs which are intended for transdermal delivery from devices such as those set forth in FIGS. 1, 5 and 6 is the compound having the structure:

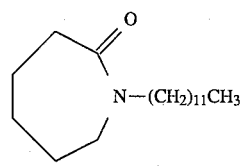

known as AZONE® marketed by the Nelson Research and Development Co. The composition comprising PVC and the compound having the structure:

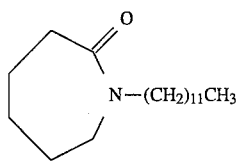

is a novel composition of matter.

Mixtures of known plasticizers can be used. The term "primary plasticizer" as used herein refers to a plasticizer which can be used alone to effect plasticization and is highly compatible with PVC at high concentrations, such as, for example, 150 parts per hundred. Primary plasticizers are contrasted with "secondary plasticizers" which, because of limited compatibility with PVC, cannot be used alone. See, Kirk-Othmer Encyclopedia of Chemical Technology, Volume 23, 3rd Edition, especially pages 913 and 914 for a discussion of primary and secondary plasticizers, which is incorporated by reference herein.

The primary plasticizer generally is present in an amount of 20 to 85 weight percent, preferably 20 to 70% based on the total weight of the plasticized PVC layer.

The plasticized PVC (preferably the PVC "plastisol") may optionally contain other additives or "excipients" useful in the practice of this invention, for example, material which enhance skin penetrated of the pharmacologically-active substances (e.g., 1,6-hexanediol and n-decyloleate) and thickeners, e.g., silica (preferably "fumed" silica, for example, AEROSIL® in an amount of from 1–6% of the layer).

With reference to FIG. 1, a blended PVC plastisol (the preferred form of the plasticized PVC) containing, for example, PVC, DOP and nitroglycerin is then coated at a rate of about 36 ounces/yd$^2$ on a backing, and then fused into solid plastisol layer 2. The backing may be a single layer of drug impermeable plastic or other material, but is referably composed of two layers 3 and 4. Layer 3 may be MYLAR® (polyester produced from ethylene glycol and phthalic anhydride) about 0.5 mils thick, and layer 4 may be PVC, about 4 mils thick. The backing 3, 4 substantially blocks loss of drug from the plastisol layer 2 other than in the direction of the surface which, in use, will contact the patient's skin.

The blended plastisol which is coated on the backing can be fused into a homogeneous solid by heating it for a short period, such as 15 to 30 second, at a temperature of, for example, 250° to 280° F. The use of a plastisol to form solid layer 2 enables layer 2 to be formed by using a low temperature for a short period of time, and provides conditions which do not affect the stability of the pharmacologically-active agents.

A strip of solid plastisol layer 2 and backing 3, 4 is then bonded to a pressure-sensitive adhesive layer 5 which, in turn, is provided with a non-adhesive backing 6 such as one made of plastic, moisture-proof fabric, aluminum foil, etc.

When not in use, the entire surface intended for skin contact is preferably covered with a release paper 7 or the like which is removed to expose surfaces of the adhesive layer 5 and drug containing plastisol layer 2 for application to the patient's skin.

FIG. 2 shows a plan view of a strip of material 20 during the stage of manufacture at which a strip of the plastisol 2 (backing 3, 4 not shown) has been applied to the adhesive tape (backing 6 not shown). For the preferred device for the controlled administration of pharmacologically-active agent, e.g., indomethacin, isosorbide dinitrate, nicotine, clonidine, glyceryl trinitrate, guanfacine or prostaglandin, a plastisol strip preferably about one inch (1") in width is applied on a two and one-half inch (2½") wide pressure-sensitive adhesive strip.

FIG. 3 shows a plan view of a strip of the material 30 in accordance with this invention; spaced lines 31 may be embossed or printed on the surface away from skin contact so that the patient may conveniently measure out and cut off the proper amount of tape device to provide the prescribed daily dosage. For a device for administering the pharmacologically-active agent, e.g., nitroglycerin, for example, a segment 1" long cut from the longer tape (resulting in an approximately one square inch (1 sq. in.) of active surface against the patient's skin) will provide a dosage of about 17 mg/24 hours; this is believed to be an enhanced rate of delivery compared with commercially available transdermal drug delivery devices and also will provide the patient with a bandage device having a surface area much smaller than found in previously available devices.

Referring to FIG. 4, the components of embodiment 33 are backing layer 34, a reservoir layer 35 that contains supplies of percutaneous absorption enhancer and pharmacologically-active substance, such as indomethacin, a diffusion membrane layer 36 and a peripheral ring 37 of contact adhesive. The diffusion membrane layer may be composed of a polymer, such as a copolymer of ethylene and methyl acrylate with the methyl acrylate being in the range of 2–90% by weight of the polymer, or blends of such copolymer with low density polyethylene, high density polyethylene or linear low density polyethylene. The contact adhesive component of embodiment 33 is in the form of a peripheral ring. Optionally, backing layer 34 may also be a semipermeable membrane. Neither the pharmacologically-active agent, e.g., isosorbide dinitrate nor enhancer passes through ring 37 and it therefore need not be permeable to those compositions. Optionally, the contact adhesive may be attached directly to the membrane 36, in which case the adhesive is selected so that it is permeable to the active agent.

Secondly, the basal surface from which the pharmacologically-active substance and enhancer (e.g., AZONE®) is transferred to the skin is defined by diffusion membrane layer 36. The backing layer is not flat but instead forms a pocket or cavity in which the reservoir layer is held. The outer edge of the backing layer is sealed to the peripheral ring of the contact adhesive as more specifically set forth in U.S. Pat. No. 4,379,454 issued on Apr. 12, 1983, the disclosure of which in incorporated herein by reference. Similarly, an article Within the contemplation of our invention need not have a matrix as is illustrated in FIG. 5 wherein the backing 61 totally surrounds the PVC-plastisol-plasticizer matrix 62 and is firmly in placed as with an adhesive on the skin 63.

As shown in FIG. 6, the device of the invention may conveniently be provided in the form of a tape roll 50 from which daily dosage requirements may be clipped by the patient.

The device is capable of application to humans or other animals capable of usefully absorbing drugs through the skin.

Other embodiments of our invention are those useful in, for example, U.S. Pat. Nos. 4,573,996 and 4,573,995 issued on Mar. 4, 1986, the specifications for which are incorporated by reference herein.

EXAMPLE I

A plastisol was formed by mixing 54% of a polyvinyl chloride resin sold under the designation FPC 6338 by Occidental Chemical Corp. and having a particle size between 1 and 5 microns, 36% DOP, and 10% nitroglycerin. The product was coated onto 1 mil polyester (MYLAR) film and cured at 280° F. The final product consisted of 8.8% nitroglycerin, 31.8% DOP, 47.8% FPC 6338, 11.6% polyester. This product can be used for delivery of nitroglycerin percutaneously.

EXAMPLES II–XIX

FUSED PLASTISOL DRUG RESERVOIR EXAMPLES

Fused plastisol drug reservoirs having variable PVC:plasticizer ratios were prepared by heating cast films of the drug containing plastisols at 290° F. for 60 seconds. The drugs used were isosorbide dinitrate (ISDN) and nicotine. AZONE® having the structure:

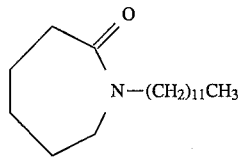

Figure 12:
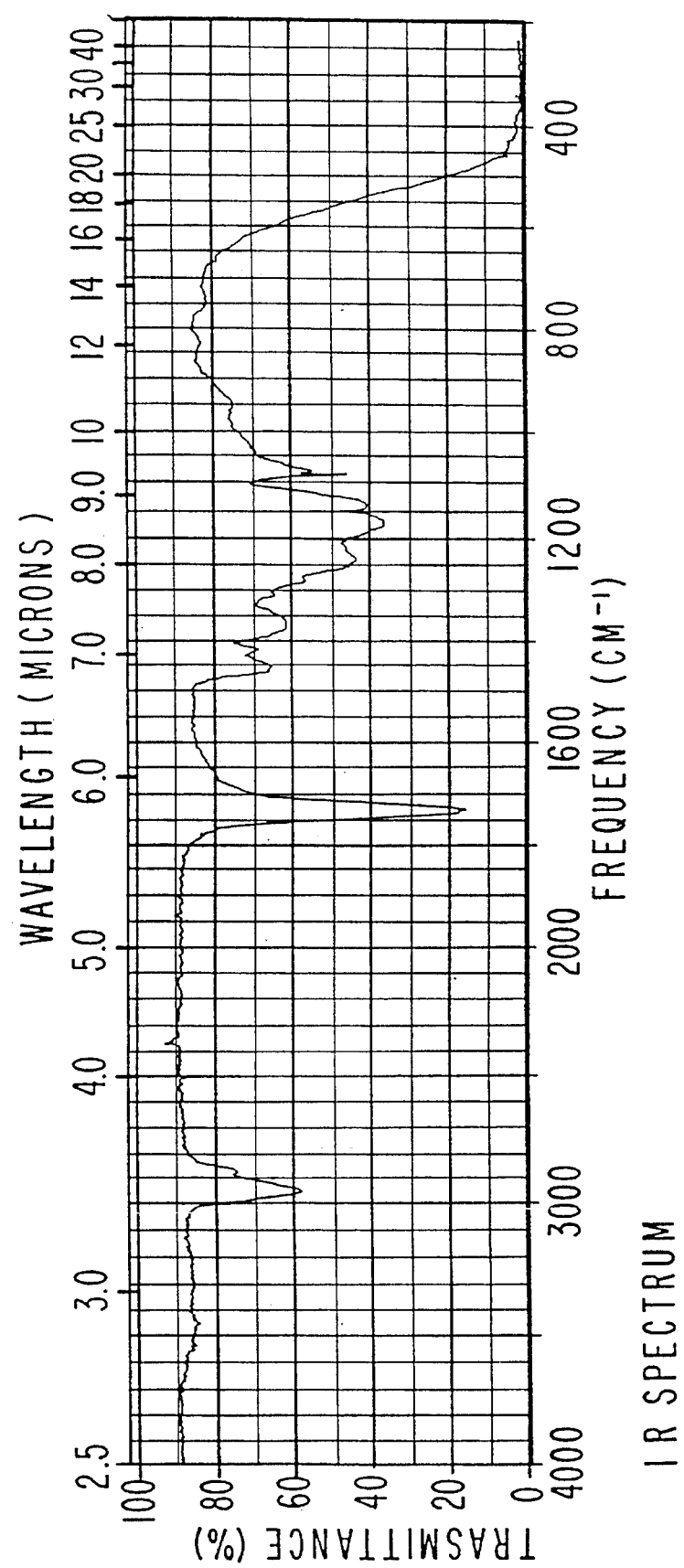

(registered trademark of the Nelson Research and Development Co.) and ADMEX® (which is a high molecular weight (MW=8000) phthalate plasticizer manufactured by the Sherex Division of Nuodex Inc.) were used as primary plasticizers in the case of the ISDN and the nicotine reservoirs, respectively. The films, thus prepared, were optically transparent. FIG. 12 is the infrared spectrum of ADMEX® 760.

The stress-strain properties of the films were determined employing standard procedures using Instron Universal Testing Instrument. The ability of the reservoir to release the drug was evaluated by measuring the dissolution rate of the drug in a fluid medium (receptorphase) when a known surface area of the drug reservoir film was exposed to an excess of the receptor phase at 31° C. The dissolution rate studies were conducted using a Franz diffusion cell. The receptor phase for the nicotine study was pH 4.0 citric acid buffer solution (an aqueous solution containing 1.2% citric acid and 1.1% disodium hydrogen phosphate), and that for the ISDN study was an aqueous solution containing 20% polyethylene glycol 400. The dissolution rate of the drug was calculated from the change in concentration of the drug in the receptor phase at different time intervals. The nicotine and ISDN concentrations were determined by ultraviolet spectroscopy and high pressure liquid chromatographic procedures, respectively.

EXAMPLES II–VII

In the following formulations (A–E in each of Examples II–VII), the following terms have the following meanings as now given:

| | |
|---|---|
| ISDN: | Isosorbide dinitrate having the structure: 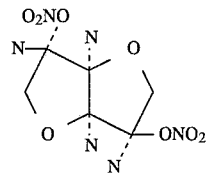 |
| AZONE: | The compound having the structure: 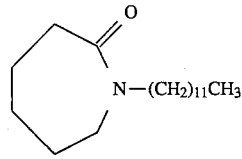 |
| 6338: | A vinyl chloride vinyl acetate copolymer having a vinyl acetate content of 4.0–4.5% manufactured by the Occidental Chemical Corporation. |
| ADMEX: | A high molecular weight (MW = 8000) phthalate plasticizer manufactured by the Sherex Division of Nuodex Inc. |
| Nicotine: | The compound having the structure: 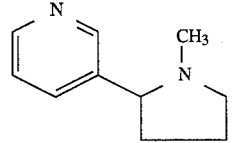 |
| Indomethacin: | The compound having the structure: 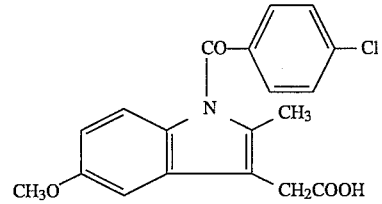 |
| Clonidine: | The compound having the structure: 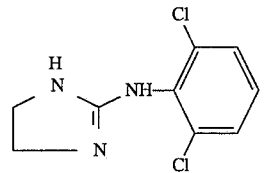 |
| GTN: | Glyceryl trinitrate |
| Guan.: | Guanfacine having the structure: |

-continued

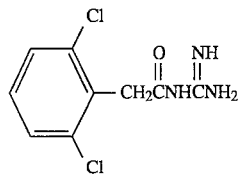

DOP: Dioctyl phthalate.
HG: 1,6-Hexylene glycol.
Cer 140: "Ceraphyl 140" being n-decyl oleate.

EXAMPLE II

| ISDN FORMULATIONS: | | | | | |
|---|---|---|---|---|---|
| | "A" | "B" | "C" | "D" | "E" |
| ISDN | 15.0% | 15.0% | 15.0% | 15.0% | 15.0% |
| AZONE | 59.5% | 51.0% | 42.5% | 34.0% | 25.5% |
| 6338 | 25.5% | 34.0% | 42.5% | 51.0% | 59.5% |

EXAMPLE III

| NICOTINE FORMULATIONS: | | | | | |
|---|---|---|---|---|---|
| | "A" | "B" | "C" | "D" | "E" |
| Nicotine | 30.0% | 30.0% | 30.0% | 30.0% | 30.0% |
| ADMEX | 49.0% | 42.0% | 35.0% | 28.0% | 21.0% |
| 6338 | 21.0% | 28.0% | 35.0% | 42.0% | 49.0% |

EXAMPLE IV

| INDOMETHACIN FORMULATIONS: | | | | | |
|---|---|---|---|---|---|
| | "A" | "B" | "C" | "D" | "E" |
| Indomethacin | 15.0% | 15.0% | 15.0% | 15.0% | 15.0% |
| AZONE | 25.5% | 34.0% | 42.5% | 51.0% | 55.0% |
| 6338 | 59.5% | 51.0% | 42.5% | 34.0% | 30.0% |

EXAMPLE V

| CLONIDINE FORMULATIONS: | | | | | |
|---|---|---|---|---|---|
| | "A" | "B" | "C" | "D" | "E" |
| Clonidine | 20.0% | 20.0% | 20.0% | 20.0% | 20.0% |
| ADMEX | 60.0% | 55.0% | 50.0% | 45.0% | 41.0% |
| 6338 | 20.0% | 25.0% | 30.0% | 35.0% | 44.0% |

EXAMPLE VI

| GTN FORMULATIONS: | | | | | |
|---|---|---|---|---|---|
| | "A" | "B" | "C" | "D" | "E" |
| GTN | 8.0% | 8.0% | 8.0% | 8.0% | 8.0% |
| ADMEX | 62.0% | 53.0% | 46.0% | 39.0% | 32.0% |
| 6338 | 30.0% | 39.0% | 46.0% | 53.0% | 60.0% |

EXAMPLE VII

| GUANFACINE FORMULATIONS: | | | | | |
|---|---|---|---|---|---|
| | "A" | "B" | "C" | "D" | "E" |
| Guan. | 30.0% | 30.0% | 30.0% | 30.0% | 30.0% |
| DOP | 25.0% | 21.0% | 18.0% | 14.0% | 10.0% |
| HG | 12.5% | 12.5% | 12.5% | 12.5% | 12.5% |
| Cer 140 | 12.5% | 12.5% | 12.5% | 12.5% | 12.5% |
| 6338 | 20.0% | 24.0% | 27.0% | 31.0% | 35.0% |

NOTE: The hexylene glycol enhances the permeability transdermally of the guanfacine. The Cer 140 adjusts the activity of the guanfacine in the reservoir.

EXAMPLES VIII–XIII

In the following examples, the following terms have meanings as given herein:

ISDN: Isosorbide dinitrate having the structure:

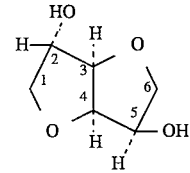

Nicotine: The compound having the structure:

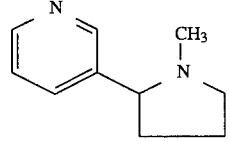

Indomethacin: The compound having the structure:

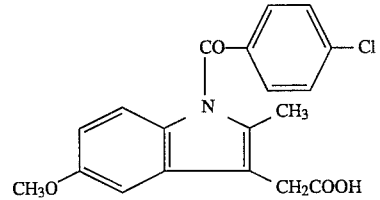

Clonidine: The compound having the structure:

-continued

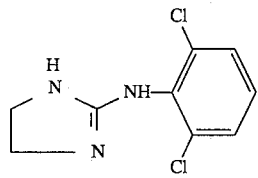

GTN:Glyceryl trinitrate.
Guan.:Guanfacine having the structure:

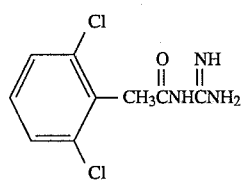

Figure 7:
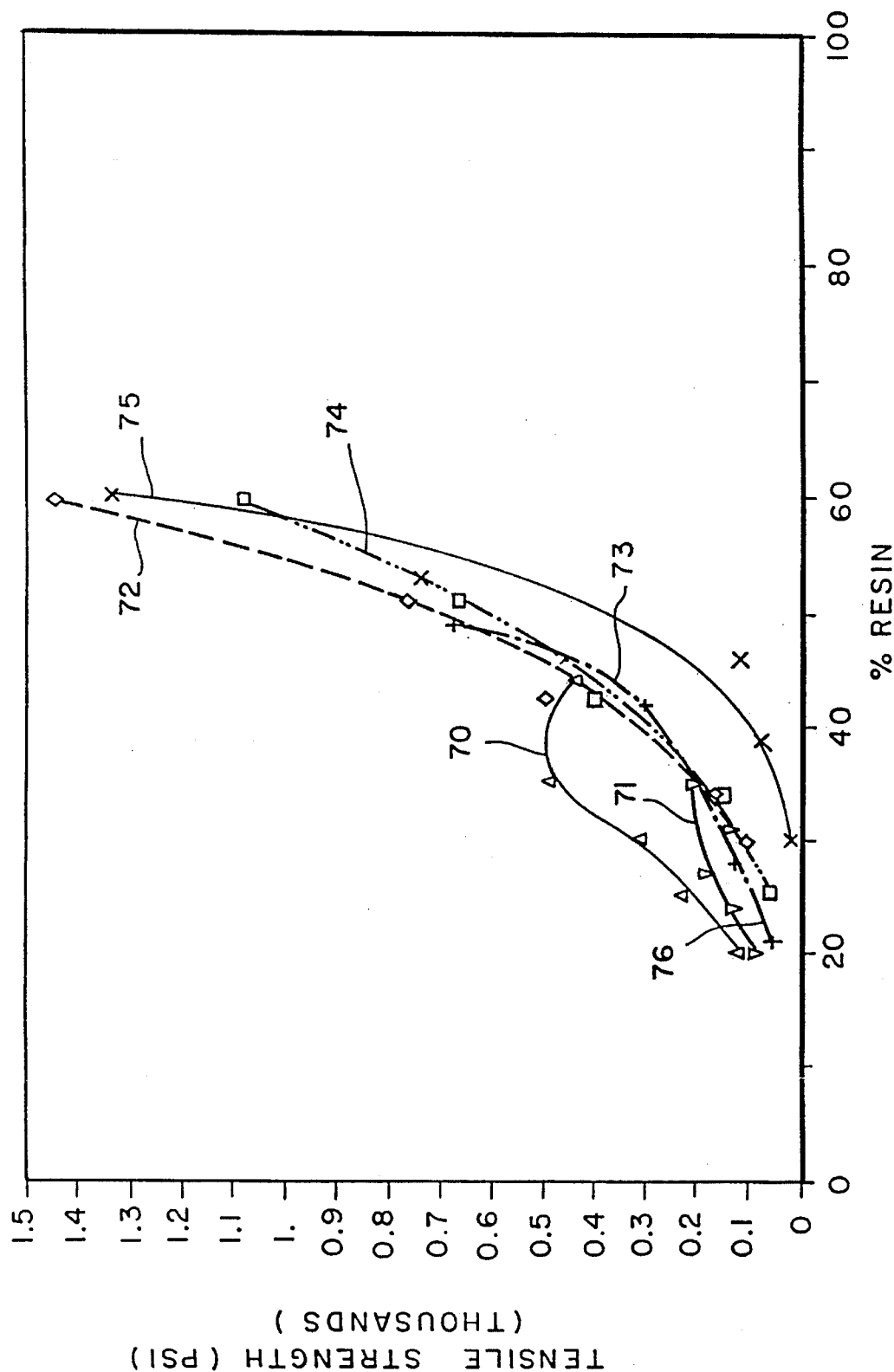
FIG. 7 is a graph of tensile strength (PSI) versus percent resin containing either of isosorbide dinitrate, nicotine, indomethacin, clonidine, glyceryl trinitrate or guanfacine, specifically as described herein in the description of Examples VIII–XIII, infra.

FIG. 7 shows tensile strength versus percent resin for each of the above formulations, The curve indicated by reference numeral 70 is the curve for clonidine. The curve indicated by reference numeral 71 is the curve for guanfacine. The curve indicated by reference 72 is the curve for indomethasin. The curve indicated by reference numeral 73 is the curve for nicotine, The curve indicated by reference numeral 74 is the curve for isosorbide dinitrate, The curve indicated by reference numeral 75 is the curve for glyceryl trinitrate.

EXAMPLE VIII

| ISDN: | |
|---|---|
| % RESIN | TENSILE STRENGTH |
| 25.5 | 57.21 |
| 34.0 | 144.09 |
| 42.5 | 399.54 |
| 51.0 | 663.81 |
| 59.5 | 1077.53 |

EXAMPLE IX

| NICOTINE: | |
|---|---|
| % RESIN | TENSILE STRENGTH |
| 21.0 | 54.22 |
| 28.0 | 125.51 |
| 35.0 | 204.39 |
| 42.0 | 300.57 |
| 49.0 | 671.30 |

EXAMPLE X

| INDOMETHACIN: | |
|---|---|
| % RESIN | TENSILE STRENGTH |
| 30.0 | 99.63 |
| 34.0 | 162.00 |
| 42.5 | 495.00 |
| 51.0 | 764.00 |

-continued

| INDOMETHACIN: | |
|---|---|
| % RESIN | TENSILE STRENGTH |
| 59.5 | 1447.00 |

EXAMPLE XI

| CLONIDINE: | |
|---|---|
| % RESIN | TENSILE STRENGTH |
| 20.0 | 118.36 |
| 25.0 | 288.70 |
| 30.0 | 308.99 |
| 35.0 | 487.65 |
| 44.0 | 440.16 |

EXAMPLE XII

| GTN: | |
|---|---|
| % RESIN | TENSILE STRENGTH |
| 30.0 | 17.53 |
| 39.0 | 74.90 |
| 46.0 | 116.43 |
| 53.0 | 738.85 |
| 60.0 | 1339.02 |

EXAMPLE XIII

| GUAN.: | |
|---|---|
| % RESIN | TENSILE STRENGTH |
| 20.0 | 84.83 |
| 24.0 | 128.40 |
| 27.0 | 180.50 |
| 31.0 | 131.50 |
| 35.0 | 203.21 |

EXAMPLES XIV–XIX

In the following examples, the following terms have meanings as set forth below:

ISDN:Isosorbide dinitrate having the structure:

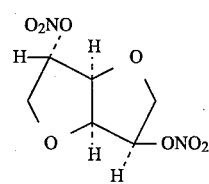

Nicotine:The compound having the structure:

-continued

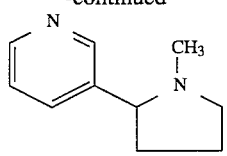

Indomethacin: The compound having the structure:

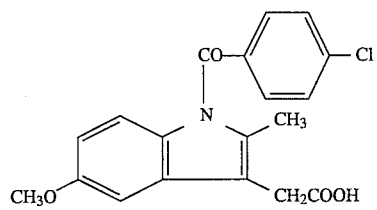

Clonidine: The compound having the structure:

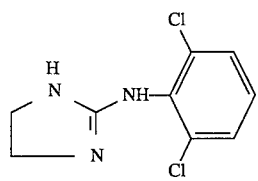

GTN: Glyceryl trinitrate.
Guan.: Guanfacine having the structure:

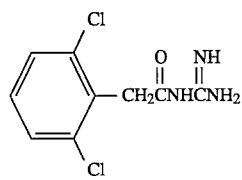

EXAMPLE XIV

| ISDN: | |
|---|---|
| % RESIN | RELEASE |
| 25.5 | 91.66 |
| 34.0 | 108.90 |
| 42.5 | 93.50 |
| 51.0 | 65.71 |
| 59.5 | 50.29 |

EXAMPLE XV

| NICOTINE: | |
|---|---|
| % RESIN | RELEASE |
| 21.0 | 40.76 |
| 28.0 | 122.78 |
| 35.0 | 218.25 |
| 42.0 | 243.55 |
| 49.0 | 216.18 |

EXAMPLE XVI

| INDOMETHACIN: | |
|---|---|
| % RESIN | RELEASE |
| 30.0 | 36.14 |
| 34.0 | 87.01 |
| 42.5 | 68.75 |
| 51.0 | 24.49 |
| 59.5 | 8.65 |

EXAMPLE XVII

| CLONIDINE: | |
|---|---|
| % RESIN | RELEASE |
| 30.0 | 103.67 |
| 25.0 | 108.22 |
| 30.0 | 80.85 |
| 35.0 | 82.18 |
| 44.0 | 62.81 |

EXAMPLE XVIII

| GTN: | |
|---|---|
| % RESIN | RELEASE |
| 30.0 | 41.91 |
| 39.0 | 48.54 |
| 46.0 | 42.63 |
| 53.0 | 46.02 |
| 60.0 | 35.81 |

EXAMPLE XIX

| GUAN: | |
|---|---|
| % RESIN | RELEASE |
| 20.0 | 31.72 |
| 24.0 | 56.85 |
| 27.0 | 63.06 |
| 31.0 | 88.41 |
| 35.0 | 165.82 |

Figure 8:
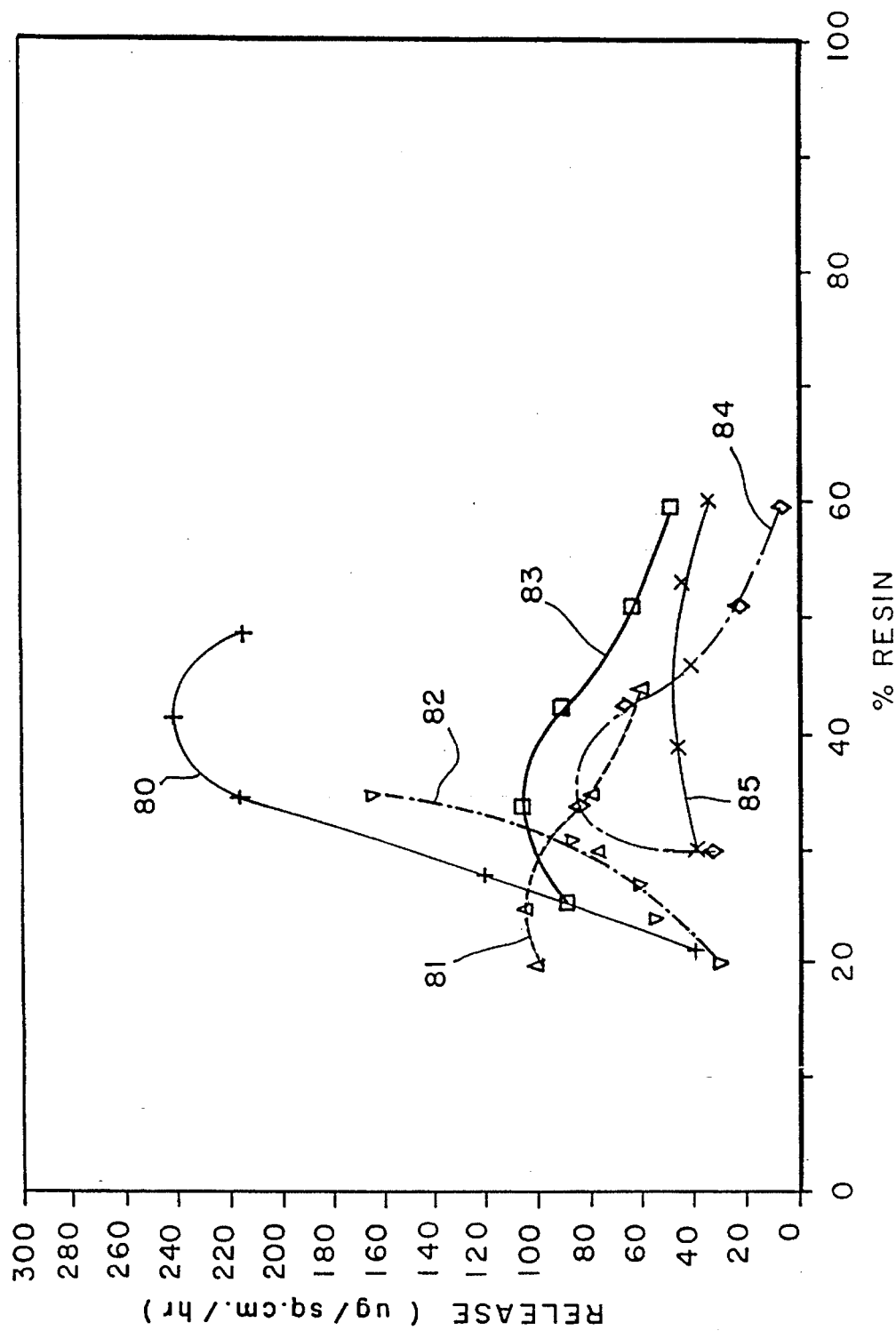
FIG. 8 is a graph showing release rate of pharmacologically-active agent (in micrograms per square centimeter per hour) versus percent resin, individually, for isosorbide dinitrate, nicotine, indomethacin, clondine, glyceryl trinitrate or guanfacine specifically in relationship to Examples XIV–XIX, infra.

FIG. 8 is a graph showing release rate in micrograms per square centimeter per hour versus percent resin. The curve indicated by reference numeral 80 is the curve for nicotine. The curve indicated by reference numeral 81 is the curve for clonidine. The curve indicated by reference numeral 82 is the curve for guanfacine. The curve indicated by reference numeral 83 is the curve for isosorbide dinitrate. The curve indicated by reference numeral 84 is the curve for indomethacin. The curve indicated by reference numeral 85 is the curve for glyceryl trinitrate.

EXAMPLE XX

TRANSDERMAL DELIVERY OF PROSTAGLANDIN FROM DRUG RESERVOIR HUMAN CLINICAL STUDY

I. Drug: Prostaglandin (American Cyanamid Co.)
Methyl (±) - (11α, 5z (and 5E), 13E, 16R (and 16S)) ethenyl-11,16 dihydroxy-9-oxoprosta-5, 13-dien-1-oate (an analog of Prostaglandin $E_2$).

II. Pharmacological Activity: Antihypertensive

| III. | Patch Formula: | |
|---|---|---|
| | PVC Resin | 59.7% |
| | Dioctyl Adipate | 38.2% |
| | 50% Prostaglandin in Dioctyl Adipate | 2.1% |

Figure 9:
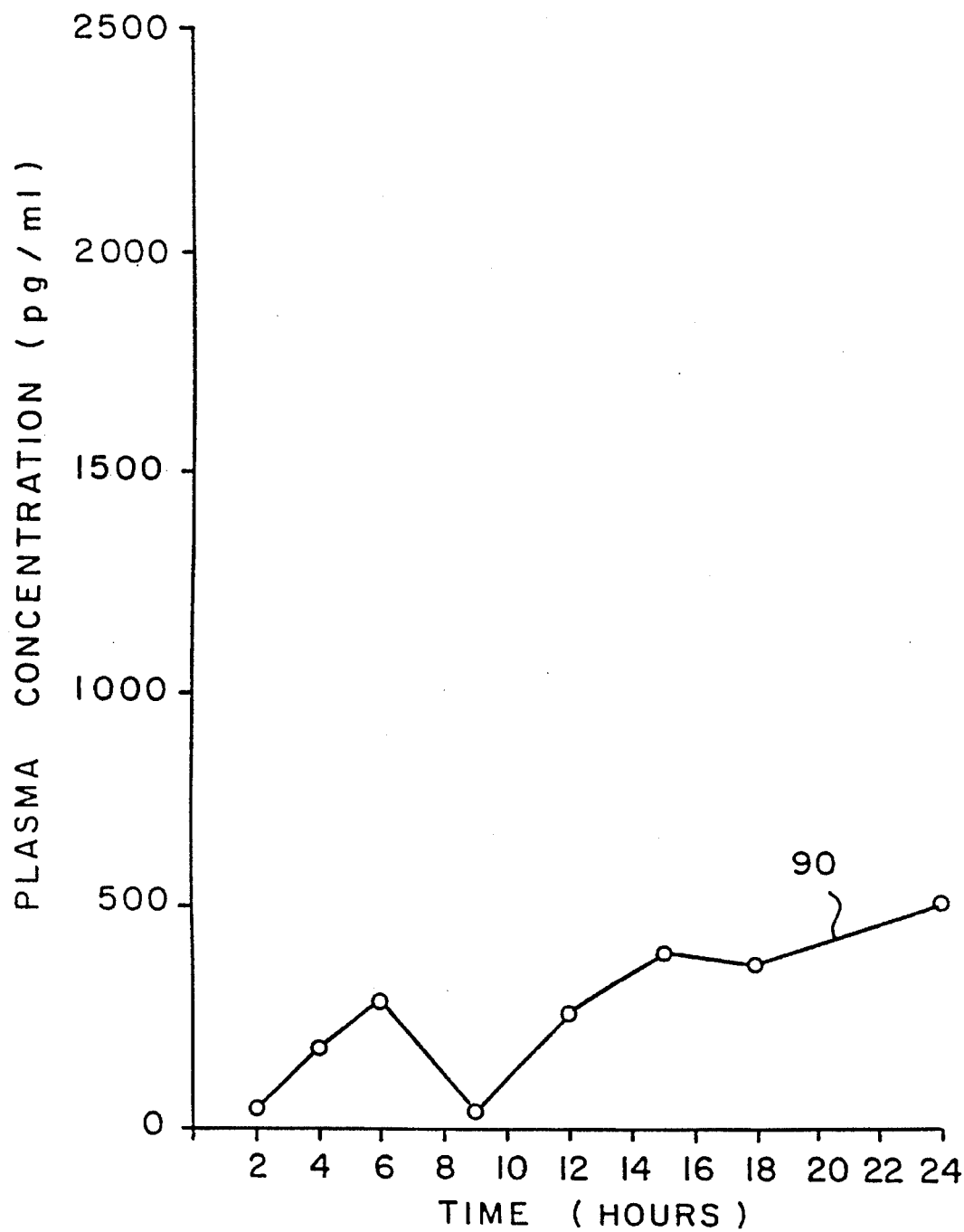
FIG. 9 is a graph of plasma concentration (picograms per milliliter) versus time detected in a human subject during the clinical study concerning the composition of matter consisting of polyvinyl chloride resin, dioctyl adipate plasticizer and prostaglandin as specifically set forth in Example XX, infra.

IV. Results:

A. The Drug Concentration up to 500 pg/ml was detected in a human subject (FIG. 9).

Figure 10:
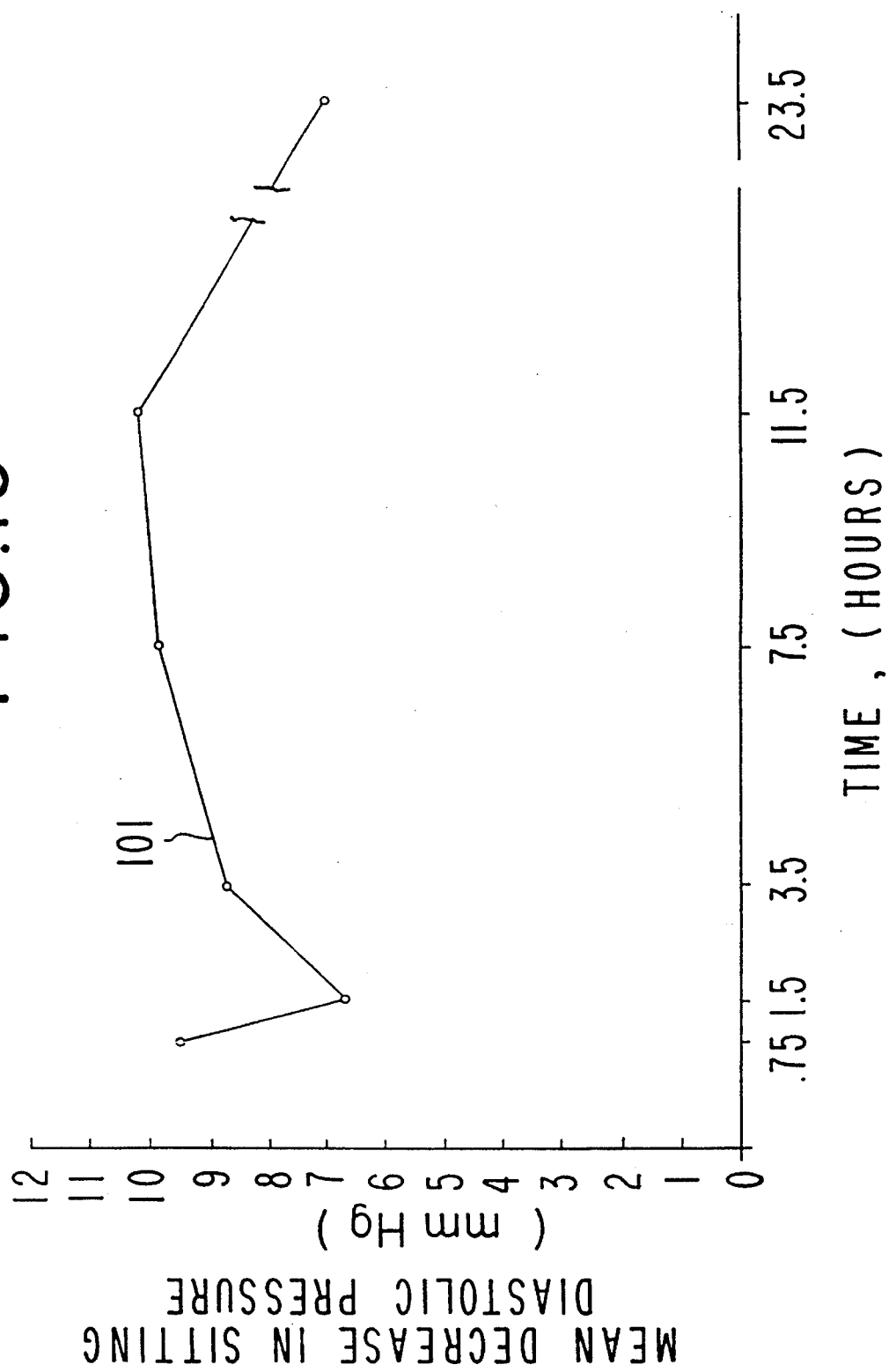
FIG. 10 is a graph showing the effective decrease in diastolic blood pressure of the human subject observed during the period of patch application as specifically set forth in Example XX.

B. Effective decrease in diastolic blood pressure of the human subject was observed during the period of patch application (FIG. 10).

The curve indicated by reference numeral 90 shows plasma concentration in picograms per ml versus time in hours. The curve indicated in FIG. 10 by reference numeral 101 shows mean decreases in sitting diastolic blood pressure following administration of the subject patch formula to normal subjects in a cross over study (sample size=15). The units of pressure are mmHg and the units of time are in hours.

EXAMPLE XXI

TRANSDERMAL DELIVERY OF NITROGLYCERIN FROM DRUG RESERVOIR - HUMAN CLINICAL STUDY

I. Drug: Nitroglycerin (Glyceryl trinitrate)

II. Pharmacological Activity: Vasodilator

| III. | Patch Formulation: | |
|---|---|---|
| | Nitroglycerin | 9.6% |
| | Dioctyl Phthalate | 76.8% |
| | PVC Resin | 9.6% |
| | Aerosil (Fumed Silica) | 4.0 |

Figure 11:
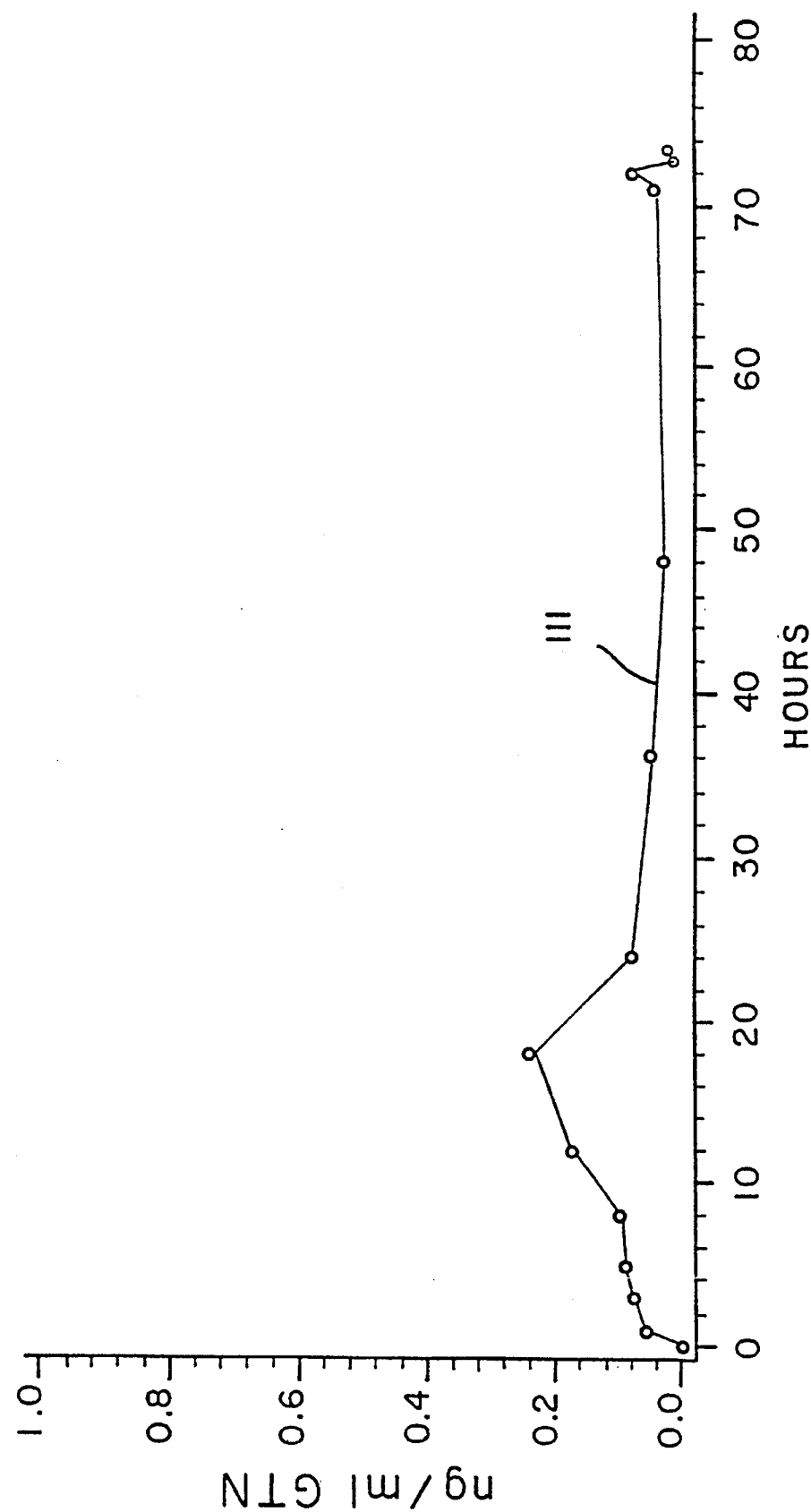
FIG. 11 is a graph of delivery of nitroglycerin versus time resulting from the use of the formulation of Example XXI.

IV. Results:

The patch delivered adequate nitroglycerin through skin of human subjects to provide a concentration of 0.1 to 0.2 ng/ml in the blood plasma for a period of 3 days as set forth in FIG. 11. The graph indicated by reference numeral 111 is a graph of delivery of glyceryl trinitrate in nanograms/ml versus time (in hours).

EXAMPLE XXII

IN VIVO TRANSDERMAL DELIVERY OF ISOSORBIDE DINITRATE (ISDN) - FROM DRUG RESERVOIR

I. Drug: Isosorbide Dinitrate (ISDN)

II. Pharmacological Activity: Vasodilator

| III. | Patch Formula: | |
|---|---|---|
| | ISDN (50% on Latose) | 15% |
| | PVC Resin | 30% |
| | AZONE ® | 32% |
| | Isopropyl Myristate | 20% |
| | Aerosil (Fumed Silica) | 3% |

IV. Test Protocol:

Formulations containing 7.5% ISDN, and 0, and 32% AZONE® respectively were tested in vivo monkeys. Each formulation was tested on two monkeys for six consecutive days. The patches were firmly placed on the shaved upper innerarm each morning and were left in place for eight hours. For each test condition blood samples of approximately 3–4 ml were withdrawn from an indwelling catheter inserted into the saphenous vein. Blood samples were drawn at 0 (prior to patch application), 4 and 8 hours after dosing. The eight-hour samples was drawn before the patches were removed. The plasma component was immediately separated from the blood by centrifugation at 1200 rpm for 5 minutes, and frozen at −20° C. The samples were then extracted to determine concentrations of ISDN and its metabolites Isosorbide 5-mononitrate (5-ISMN) and Isosorbide 2-Mononitrate (2-ISMN).

Upon removal of the patches, the site of application was washed with dilute alcohol and inspected visually. Any changes in the condition of the skin (such as erythema or edema) was scored according to the Draze Scoring System. This inspection was repeated 30 minutes and again before next patch application.

V. Results:

The mean plasma ISDN and metabolite results for the patches are shown in Table I. An increase of 300% to 400% in plasma ISDN concentration was observed for patches containing 32% AZONE®.

A maximum of 43.8% ng/ml of plasma ISDN was obtained from 2 patches with a total surface area of 12.5 cm. However, the data did not suggest that there was a linear increase of plasma level with surface area of patch. In general, doubling the patch surface area more than doubled the plasma level, for ISDN as well as the metabolites.

TABLE I

8 HOURS IN VIVO RESULTS OF ISDN PATCHES ON MONKEYS
AVERAGE CONCENTRATION (ng/ml)

| % AZONE ® | NO. OF PATCHES* | ISDN | 5 ISMN | 2 ISMN |
|---|---|---|---|---|
| 0 | 1 | 3.46 | 12.75 | 3.05 |
| | 2 | 19.39 | 55.52 | 12.67 |
| 12 | 1 | 6.08 | 23.56 | 4.64 |
| | 2 | 30.23 | 68.43 | 17.11 |
| 32 | 1 | 14.14 | 42.01 | 9.75 |
| | 2 | 43.85 | 87.85 | 23.75 |

*Patch size was 6.25 cm$^2$.

What is claimed is:

1. A device for the controlled release and delivery to animal tissue of a pharmacologically-active agent comprising an impermeable backing layer, a plasticized polyvinyl chloride layer, and an adhesive layer, said plasticized polyvinyl chloride layer comprising by weight from about 20 up to about 60% of a polyvinyl chloride resin, from about 20 up to about 70% of plasticizer and from about 0.5 up to about 35% of said pharmacologically-active substance which when a surface of said plasticized polyvinyl chloride layer is in contact with a tissue either exterior to the epidermis or subdermally or in contact with a tissue of an animal to be treated with said pharmacologically-active agent, said pharmacologically-active agent is absorbed into and through said tissue and thence into circulatory system of said animal, said pharmacologically-active agent being uniformly dispersed in said plasticized polyvinyl chloride layer in an amount such that an effective amount of said pharmacologically-active agent is absorbed into said animal in a prescribed period of time wherein the pharmacologically-active agent is selected from the group consisting of isosorbide dinitrate, nicotine, indomethacin, clonidine, glyceryl trinitrate, quanfacine and prostaglandin.

2. The device of claim 1 wherein at least one control membrane for secondary control of release is attached on one side of said device.

3. The device of claim 1 wherein the plasticizer is a polymeric plasticizer.

4. The device of claim 1 wherein the plasticizer is a monomeric plasticizer.

5. The device of claim 1 wherein the plasticizer is dioctyl phthalate.

6. The device of claim 3 wherein the polymeric plasticizer is a polyadipate.

7. The device of claim 3 wherein the polymeric plasticizer is epoxidized soybean oil.

8. The device of claim 2 wherein the polyvinyl chloride is present in an amount of about 30–60%, the plasticizer is present in an amount of about 30–60% and the pharmacologically-active agent is present in an amount of about 0.5–35%.

9. The device of claim 1 in the form of an elongated tape.

10. The device of claim 9 wherein said plasticized polyvinylrchloride is a plastisol and the plastisol layer comprises polyvinyl chloride resin, a polymeric plasticizer or a monomeric plasticizer and a pharmacologically-active agent selected from the group consisting of isosorbide dinitrate, nicotine, indomethacin, clonidine, glyceryl trinitrate, guanfacine and prostaglandin.

11. The device of claim 1 wherein said polyvinyl chloride is present in an amount of about 30–60%, said plasticizer is present in an amount of about 30–60% and said pharmacologically-active agent is present in an amount of from about 0.5 up to about 35%.

12. The device of claim 11 wherein the pharmacologically-active agent is nitroglycerin and the nitroglycerin is present in an amount of about 20–35%.

13. The device of claim 9 wherein said tape is provided with indicia indicating the length of a segment of said tape which is adequate to administer a prescribed dosage of said pharmacologically-active substance.

14. The device of claim 9 in the form of a roll of tape of sufficient length to provide multiple tape segments adequate to provide a prescribed dosage of said pharmacologically-active agent.

15. A device for the controlled release and transdermal delivery of a pharmacologically-active agent comprising a solid plasticized polyvinyl chloride layer comprising by weight from about 20 up to about 60% of a polyvinyl chloride resin; from about 20 up to about 70% of a plasticizer and from about 0.5 up to about 35% of a pharmacologically-active agent which, when a surface of said layer is in contact with the skin of an animal to be treated with said pharmacologically-active agent, is absorbed into and through the skin and thence into the circulatory system of said animal, said pharmacologically-active agent being uniformly dispersed in said plasticized polyvinyl chloride layer in an amount such that an effective amount of the pharmacologically-active agent is absorbed through the skin of said animal in a prescribed period of time, a backing layer covering the surface of said plasticized polyvinyl chloride layer opposite the skin contacting surface of said plasticized polyvinyl chloride layer, said backing layer forming a barrier substantially blocking release of said pharmacologically-active agent from the surface of said plasticized polyvinyl chloride layer opposite the skin contacting surface, and means for maintaining the skin contacting surface of said plasticized polyvinyl chloride layer in contact with the skin of said animal so that transdermal absorption of said pharmacologically-active agent takes place, wherein the pharmacologically-active agent is selected from the group consisting of isosorbide dinitrate, nicotine, indomethacin, clonidine, glyceryl trinitrate, guanfacine and prostaglandin.

16. The device of claim 15 wherein a rate controlling membrane is attached to the plasticized polyvinyl chloride layer on the side of the plasticized polyvinyl chloride layer opposite to the backing layer.

17. The device of claim 15 or 16 wherein the means for maintaining the skin contacting surface of said plasticized polyvinyl chloride layer in contact with the skin is a pressure sensitive adhesive adhered to the plasticized polyvinyl chloride layer on the side of the plasticized polyvinyl chloride layer opposite said backing layer.

18. The device of claim 15 or 16 wherein the means for maintaining the skin contacting surface of said plasticized polyvinyl chloride layer in contact with the skin is a pressure sensitive adhesive layer adhered to the side of the backing layer opposite the plasticized polyvinyl chloride layer and extending beyond the periphery of the plasticized polyvinyl chloride layer.

19. The device of claim 15 or 16 wherein said plasticized polyvinyl chloride is a polyvinyl chloride plastisol and said plasticizer is a polymeric plasticizer or a monomeric plasticizer.

20. The device of claim 19 wherein the polymeric plasticizer is a polyadipate.

21. The device of claim 19 wherein the plasticizer is dioceyl phthalate.

22. The device of claim 19 wherein the polymeric plasticizer is epoxidized soybean oil.

23. The device of claim 15 or 16 wherein said polyvinyl chloride is present in an amount of about 30–60%, said plasticizer is present in an amount of about 30–60%, and said pharmacologically-active agent is present in an amount of about 0.5–35%.

24. The device of claim 17 in the form of an elongated tape.

25. The device of claim 24 wherein the plasticizer is a polymeric plasticizer.

26. The device of claim 25 wherein said polyvinyl chloride is present in an amount of about 30–60%, said plasticizer is present in an amount of about 30–60%, and said pharmacologically-active agent is present in an amount of about 0.5–35%.

27. The device of claim 24 wherein said tape is provided with indicia indicating the length of a segment of said tape which is adequate to administer a prescribed dosage of said pharmacologically-active agent.

28. The device of claim 24 in the form of a roll of tape of sufficient length to provide multiple tape segments adequate to provide a prescribed dosage of said drug.

29. The device of claim 1 wherein the plasticizer is the compound having the structure:

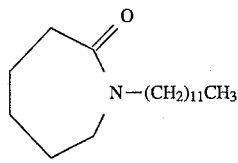

30. The device of claim 1 wherein the plasticizer is N,N-diethyltoluamide.

31. The device of claim 2 or 16 wherein the rate controlling membrane comprises an ethylene-methyl acrylate copolymer having 2–90% by weight of methyl acrylate monomeric units.

32. A device for the controlled release and delivery to animal tissue of a pharmacologically-active agent comprising an impermeable backing layer, a plasticized polyvinyl chloride layer, and an adhesive layer, said plasticized polyvinyl chloride layer comprising by weight from about 20 up to about 60% of a polyvinyl chloride resin, from about 20 up to about 70% of plasticizer and from about 10 up to about 35% of said pharmacologically-active substance which when a surface of said plasticized polyvinyl chloride layer is in contact with a tissue either exterior to the epidermis or subdermally or in contact with a tissue of an animal to be treated with said pharmacologically-active agent, said pharmacologically-active agent is absorbed into and through said tissue and thence into circulatory system of said animal, said pharmacologically-active agent being uniformly dispersed in said plasticized polyvinyl chloride layer in an amount such that an effective amount of said pharmacologically-active agent is absorbed into said animal in a prescribed period of time.

* * * * *